United States Patent
Kamal et al.

(10) Patent No.: US 8,383,373 B2
(45) Date of Patent: Feb. 26, 2013

(54) PROCESS FOR PREPARING LONG-CHAIN DICARBOXYLIC ACIDS

(75) Inventors: Ahmed Kamal, Andhra Pradesh (IN); Sheelu Gurrala, Andhra Pradesh (IN); Wasantrao Nitin Fadnavis, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 1015 days.

(21) Appl. No.: 12/096,091

(22) PCT Filed: Dec. 30, 2005

(86) PCT No.: PCT/IN2005/000459
§ 371 (c)(1),
(2), (4) Date: Sep. 12, 2008

(87) PCT Pub. No.: WO2007/077568
PCT Pub. Date: Jul. 12, 2007

(65) Prior Publication Data
US 2009/0305367 A1    Dec. 10, 2009

(51) Int. Cl.
*C12N 1/00* (2006.01)
*C12P 1/02* (2006.01)
*C12P 7/00* (2006.01)
*C12P 7/40* (2006.01)
*C12P 7/46* (2006.01)

(52) U.S. Cl. ........ 435/132; 435/136; 435/145; 435/171; 435/255.4; 435/255.5; 435/921; 435/938

(58) Field of Classification Search ................. None
See application file for complete search history.

(56) References Cited

U.S. PATENT DOCUMENTS

| | | | |
|---|---|---|---|
| 3,796,630 A * | 3/1974 | Wegner | 435/143 |
| 3,843,644 A * | 10/1974 | Kurihara et al. | 544/345 |
| 4,339,536 A * | 7/1982 | Kato et al. | 435/142 |
| 4,414,329 A * | 11/1983 | Wegner | 435/71.1 |
| 4,617,274 A * | 10/1986 | Wegner | 435/255.5 |
| 5,705,144 A * | 1/1998 | Harding et al. | 424/59 |
| 6,498,268 B1 * | 12/2002 | Raths | 560/200 |
| 7,122,525 B2 * | 10/2006 | Michaelis et al. | 514/29 |

FOREIGN PATENT DOCUMENTS

WO    95/21145    8/1995

OTHER PUBLICATIONS

Ulezlo, et al "Search for yeast producers of brassylic and sebacic fatty acids" *Applied Biochemistry and Microbiology* (2004) vol. 40, No. 5 pp. 460-462 XP002397011.
"Biennial Report 2003-2005", *Indian Institute of Chemical Technology*, Hyderabad, India XP002397052, Retrieved from the Internet on Aug. 30, 2006, Actual date of publication to be established.
Cao, et al "Engineering the acetyl-CoA transportation system of *Candida tropicalis* enhances the production of dicarboxylic acid" *Biotechnology Journal* (2006) vol. 1, pp. 68-74 XP002397012.

* cited by examiner

*Primary Examiner* — Debbie K Ware
(74) *Attorney, Agent, or Firm* — Ladas & Parry LLP

(57) ABSTRACT

The present invention particularly discovered strains that are capable of producing a long-chain dicarboxylic acid by culturing microorganisms belonging to *Candida vini Candida entamophila, Candida blankii* and *Pichia farinosa* which has the ability to produce a long-chain dicarboxylic acid in a liquid medium containing a straight-chain saturated hydrocarbon (tridecane) as substrate.

24 Claims, No Drawings

PROCESS FOR PREPARING LONG-CHAIN DICARBOXYLIC ACIDS

The present invention relates to an advantageous process for producing long-chain dicarboxylic acids from straight-chain hydrocarbons by utilizing the microorganisms.

BACKGROUND TO THE INVENTION

Several strains of yeast are known to excrete alpha, omega-dicarboxylic acids as a byproduct when cultured on alkanes or fatty acids as the carbon source. In particular, yeast belonging to the genus *Candida*, such as *C. albicans, C. cloacae, C. guillermondii, C. interinedia, C. lipolytica, C. maltosa, C. parapsilosis* and *C. zeylenoides* are known to produce such dicarboxylic acids (Isamu Shiio and RyousukeUchio, Agr. Biol. Chem. 1971, 35: 2033-2042). In *C. tropicalis*, the first step in the omega-oxidation pathway is catalyzed by a membrane-bound enzyme complex (omega-hydroxylase complex) comprised of a cytochrome P450 monooxygenase and an NADPH-cytochrome reductase. This hydroxylase complex is responsible for the primary oxidation of the terminal methyl group in alkanes and fatty acids (Michele Gilewicz, Marcelle Zacek, Jean-Claude Bertrand, and Edgard Azoulay, *Can. J Microbiol.*, 1979, 25, 201).

It has been established that hydrocarbon substrates are enzymatically oxidized in the yeast microsomes. Following transport into the cell, n-alkane substrates for example, are hydroxylated to fatty alcohols by a specific cytochrome P450 system. Two further oxidation steps, catalyzed by alcohol oxidase and aldehyde dehydrogenase, lead to the corresponding fatty acid. The fatty acids can be further oxidized through the same pathway to the corresponding dicarboxylic acid (Colin Ratledge, J. Am. Oil Chem. Soc., 1984, 61(2), 447-453). The di-terminal oxidation, leads to dicarboxylic acid production, from aliphatic hydrocarbons by yeasts (Shigeo Ogino, Keiji Yano, Gakuzo Tamura and Kei Arima, *Agri. Biol. Chem.*, 1965, 29(11), 1009-1015).

The omega-oxidation of fatty acids proceeds via the omega-hydroxy-fatty acid and its aldehyde derivative, to the corresponding dicarboxylic acid without the requirement for CoA activation. However, both fatty acids and dicarboxylic acids can be degraded, after activation to the corresponding acyl-CoA ester, through the β-oxidation pathway in the peroxisomes (Atsuo Tanaka and saburo Fukui, In: The Yeasts, Vol. 3, Metabolism and physiology of Yeasts, Edited by A. H. Rose and J. S. Harrison, 2$^{nd}$ Edition, Academic Press, Harcourt Brace Jovanovich, Publishers), leading to chain shortening. In yeast, beta-oxidation takes place solely in the peroxisomes (Mitsuyoshi Ueda, Kazunori Yamanoi, Tadashi Morikawa, Hirofumi Okada and Atsuo Tanaka, Agr. Biol. Chem., 1985, 49, 1821-1828).

Dicarboxylic acids produced through fermentation by most yeasts, including *C. tropicalis*, are often shorter than the original substrate by one or more pairs of carbon atoms and mixtures are common (Shigeo Ogino, Keiji Yano, Gakuzo Tamura and Kei Arima, Agr. Biol. Chem., 1965, 29(11), 1009-1015., Shio and Uchio, Agr. Biol. Chem., 1971, 35(13), 2033-2042). These undesirable by-products are often associated with biological production of dicarboxylic acids.

It is known that the formation of dioic acids can be substantially increased by the use of suitable mutants (RyousukeUchio and Isamu Shiio, *Agri. Biol. Chem.*, 1972, 36(3), 426-433). The wild-type yeasts produce little if any dicarboxylic acid. Often, mutants partially defective in their ability to grow on alkane, fatty acid or dicarboxylic acid substrates demonstrate enhanced dicarboxylic acid yields. However, these mutants have not been characterized beyond their reduced ability to utilize these compounds as a carbon source for growth. In all likelihood, their ability to produce dicarboxylic acids is enhanced by a partial blockage of the beta-oxidation pathway. Furthermore, compounds known to inhibit beta-oxidation (i.e. acrylate) also result in increased dicarboxylic acid yields.

In addition, the use of such a mutant should prevent the undesirable chain modifications associated with passage through beta-oxidation, such as unsaturation, hydroxylation, or chain shortening.

Many organisms carry out the transformations, including *Cryptococcus neoformans* and *Pseudomonas aeruginosa, Corynebacterium* sp., and at least two strains of *Candida*, that is *C. cloacae* and *C. tropicalis*. (Kenneth D. Green, Michael K. Turner, Johm M. Woodley, *Enzyme and Microbial Technology,* 2000, 27, 205-211).

The work with the bacterial cells has used wild-type organisms, in which solvents, detergents, and immobilization may all give improved conversions (E. C. Chan and J. Kuo, Biotransformation of dicarboxylic acid by immobilized *Cryptococcus* cells. *Enzyme Microb Technol,* 1997, 20, 585-589). In contrast, the work with the yeast strains has usually used mutants of *Candida tropicalis* in which the β-oxidation of fatty acids is impaired. Engineered strains of *C. tropicalis* that lack several key enzymes of β-oxidation are particularly effective catalysts for these oxidations. This directs the metabolic flux toward ω-oxidation, and the n-alkanes are more efficiently converted to the corresponding dioic acids.

OBJECTS OF THE INVENTION

The main object of the invention is to provide a process for the preparation of saturated dicarboxylic acids with improved yields and selectivity from the corresponding long chain hydrocarbon using microorganisms.

Other objects of this invention will become apparent from the following description.

SUMMARY OF THE INVENTION

The present invention provides a process for the preparation of one or more saturated dicarboxylic acids from one or more corresponding saturated hydrocarbons with the same number of carbon atoms and wherein the stereostructure of the starting compounds is maintained, comprising culturing a strain selected from the group consisting of *Candida vini, Candida entamophila, Candida blankii* and *Pichia farinosa* in a liquid medium containing the saturated hydrocarbon as substrate.

In one embodiment of the invention, the concentration of the saturated hydrocarbon substrate is between 5-15% (v/v).

In another embodiment of the invention, the liquid medium contains metal salts and organic cofactors.

In another embodiment of the invention, the culturing comprises biochemical oxidation carried out at a temperature between 20 and 35° C. and for a period of up to 3 days.

In another embodiment of the invention, the saturated hydrocarbon is a straight chain hydrocarbon with 13 carbon atoms and with a methyl group at both the terminals.

In another embodiment of the invention, the saturated dicarboxylic acid is recovered from the culture medium by any conventional means.

In another embodiment of the invention, the saturated hydrocarbon is tridecane and the corresponding saturated dicarboxylic acid produced is Brassylic acid.

In another embodiment of the invention, the process for producing a long-chain dicarboxylic acid comprises culturing a yeast strain selected from the group consisting of *Candida vini, Candida entamophila, Candida blankii* and *Pichia farinosa*, capable of assimilating straight-chain hydrocarbons in a liquid medium containing a straight-chain hydrocarbon as a substrate to obtain a fermentation broth containing a long-chain dicarboxylic acid corresponding to said hydrocarbon, and recovering said saturated long chain dicarboxylic acid.

In another embodiment of the invention, the culturing is effected under aerobic conditions.

In another embodiment of the invention, the microorganism strain is initially cultivated in a medium containing a different carbon source selected from n-decane and n-dodecane and assimilatable by the microorganism, following which the saturated hydrocarbon is added to the medium when the microorganism has grown sufficiently, and oxidation is continued, under aerobic conditions, to produce the saturated dicarboxylic acid.

In another embodiment of the invention, the pH value of the medium is in the range of 6.0 to 7.0 in the initial stage of culturing and then at 7.0 in the succeeding state of culturing.

In another embodiment of the invention, one or more yield inducers selected from the group consisting of $H_2O_2$, alkanes, and mixtures thereof are added to the liquid medium.

In another embodiment of the invention, the liquid culture medium is extracted with hexane to remove unwanted matter therein such as unreacted hydrocarbon, by-products such as monocarboxylic acid, are effectively removed leaving the said dicarboxylic acid in fermentation broth, followed by addition of an alkaline solution such selected from the group consisting of sodium hydroxide or potassium hydroxide to the fermentation broth to adjust pH of the solution to 10 to 13, preferably 11 to 12, to dissolve the dicarboxylic acid in said fermentation broth, followed by adjusting the pH of the fermentation broth to pH 2., using a mineral acid selected from the group consisting of hydrochloric acid, sulfuric acid, phosphoric acid, and bromic acid, to precipitate the dissolved dicarboxylic acid, followed by extraction of the dicarboxylic acid with ether.

In another embodiment of the invention, the culture medium for growth of the microorganism comprises 3.0 g yeast extract, 3.0 g malt extract, 5.0 g Peptone, 10 g Glucose and 1 L Distilled water, pH 7.0.

In another embodiment of the invention, the culture medium for testing for medium production of Dicarboxylic acid comprises 10 g $(NH_4)_2HPO_4$, 2 g $K_2HPO_4$, 0.3 g $MgSO_4$, 10 mg $FeSO_4.7H_2O$, 8 mg $ZnSO_4.7H_2O$, 8 mg $MnSO_4$, 9 ml Tridecane and 900 ml Distilled water, pH 7.0.

In another embodiment of the invention, the culture medium for preparation of resting cells and seed culture for fermentation comprises 20 g D-Sorbitol, 10 g $(NH_4)_2HPO_4$, 2 g $K_2HPO_4$, 0.3 g $MgSO_4$, 10 mg $FeSO_4.7H2O$, 8 mg $ZnSO_4.7H_2O$, 8 mg $MnSO_4$, 2 g Yeast extract, 100 μg of Biotin and 900 ml Distilled water, pH 7.0.

In another embodiment of the invention, the culture medium for fermentation comprises Tridecane 5% v/v, Sodium acetate 5 g, $K_2HPO_4$ 2 g, $MgSO_4$ 0.3 g, $FeSO_4.7H_2O$ 10 mg, $ZnSO_4.7H_2O$ 8 mg, $MnSO_4$ 8 mg, Yeast extract 2 g and Distilled water 900 ml, pH 7.0.

In another embodiment of the invention, the selectivity with *Pichia farinose* for brassylic acid by oxidation of tridecane is 73.81% and the percentage of conversion is 21.59.

In another embodiment of the invention, the selectivity with *Candida blankii*, for brassylic acid by oxidation of tridecane is 45.68% and the percentage of conversion is 5.22.

In another embodiment of the invention, the selectivity with *Candida vini*, for brassylic acid by oxidation of tridecane is 99.18% and the percentage of conversion is 2.80.

In another embodiment of the invention, the selectivity with *Candida entamophila*, for brassylic acid by oxidation of tridecane is 23.58% and the percentage of conversion is 28.70.

In another embodiment of the invention, the culture medium includes one or more additional nutrients selected from a nitrogen source and an inorganic salt.

In another embodiment of the invention, the nitrogen source is selected from the group consisting of peptone, urea, ammonium phosphate, ammonium chloride, ammonium sulfate and ammonium nitrate.

In another embodiment of the invention, the inorganic salt is selected from the group consisting of phosphates, sulfates and hydrochlorides of sodium, potassium, magnesium, iron, nickel and zinc, selected in turn respectively from the group consisting of $KH_2PO_4$, $K_2HPO_4$, $Na_2HPO_4.12H_2O$, $MgSO_4 7H_2O$, $FeSO_4.7H_2O$, $ZnSO_4.7H_2O$ and NaCl.

In another embodiment of the invention, one or more conventional nutrients selected from the group consisting of yeast extract, meat extract and D-biotin are added to the culture medium for assisting the growth of the yeast.

DETAILED DESCRIPTION OF THE INVENTION

Disclosed in this invention is a process for producing a long-chain dicarboxylic acid by culturing microorganisms belonging to *Candida vini Candida entamophila, Candida blankii* and *Pichia farinosa* which have the ability to produce a long-chain dicarboxylic acid in a liquid medium containing a straight-chain saturated hydrocarbon (tridecane) as substrate.

This invention relates to a process for the preparation of a said saturated dicarboxylic acid from a saturated hydrocarbon, by the use of said yeast strains.

In an embodiment of the present invention, for producing a long-chain dicarboxylic acid which comprises culturing a yeast belonging to *Candida vini Candida entamophila, Candida blankii* and *Pichia farinosa*, capable of assimilating straight-chain hydrocarbons in a liquid medium containing a straight-chain hydrocarbon as substrate to obtain a fermentation broth containing a long-chain dicarboxylic acid corresponding to said hydrocarbon.

The carbon source that is employed as the starting material for the preparation of saturated dicarboxylic acid is a saturated hydrocarbon having 13 carbon atoms.

According to the invention, the saturated hydrocarbon is employed as the carbon source for the cultivation of the aforementioned microorganism, under aerobic conditions, to produce a saturated dicarboxylic acid having 13 carbon atoms. Alternatively, the microorganism can be initially cultivated in a medium containing a different carbon source assimilable by the microorganism, rather than the above-mentioned saturated hydrocarbon, such as n-decane, n-dodecane. The said saturated hydrocarbon is then added to the medium when the microorganism has grown sufficiently, and cultivation is continued, under aerobic conditions, to produce the saturated dicarboxylic acid.

In yet another embodiment of the present invention, resting cells of the aforementioned yeasts can be employed for the preparation of the saturated dicarboxylic acid in the following manner. First, the microorganism is cultivated in a medium containing a carbon source assimilable by the microorganism and different than the saturated hydrocarbon, i.e., the starting compound. Subsequently, the microorganism is cultivated in a medium containing a saturated hydrocarbon i.e., medium B which is the testing medium for the production of dicarboxylic acid, thus-cultivated microorganism is transferred to medium D, for preparation of resting cells and seed culture for fermentation experiments. The resting cells are employed for the enzymatic oxidation of the said saturated hydrocarbon to obtain the saturated dicarboxylic acid. This reaction can be carried out by suspending the microorganism, after it has been removed from the medium D and addition of an appropriate amount of the saturated hydrocarbon for medium E, the fermentation medium. In the process where the resting cells of the microorganism are used, the cultivation of the microorganism and the oxidation of the said saturated hydrocarbon can be conducted separately. In the oxidation step, the said microorganism can no longer be cultivated because of no carbon source. The said starting material used in the oxidation step, the saturated hydrocarbon, is not used for cultivation of the microorganism.

The said saturated hydrocarbon is preferably maintained in contact with the aqueous phase and the microorganism by vigorous stirring or shaking which is generally satisfactory, because the said saturated hydrocarbon is a liquid. If needed, sufficient contact can be accomplished by addition of a surface active agent or the like.

The cultivation process of the invention is carried out in a medium containing the aforementioned carbon source and other conventional nutrients, such as a nitrogen source and an inorganic salt. Examples of suitable nitrogen sources include organic and inorganic nitrogen-containing compounds, such as peptone, urea, ammonium phosphate, ammonium chloride, ammonium sulfate and ammonium nitrate. Examples of the inorganic salts include phosphates, sulfates and hydrochlorides of sodium, potassium, magnesium, iron, nickel and zinc, such as $KH_2PO_4$, $K_2HPO_4$, $Na_2HPO_4.12H_2O$, $MgSO_4 7H_2O$, $FeSO_4.7H_2O$, $ZnSO_4.7H_2O$ and NaCl. Moreover, other nutrients, such as yeast extract, meat extract and D-biotin, can be added to the medium for assisting the growth of the yeast.

The cultivation is carried out at room temperature or at a temperature slightly higher than room temperature. A temperature in the range of 20° C. to 35° C. is preferred. The pH of the medium is within the range of 6.0 to 7.0 in the initial stage of culturing and then at 7.0 in the succeeding state of culturing, the pH is adjusted by addition of a neutralizing agent, such as ammonia, sodium hydroxide or potassium hydroxide.

The cultivation is, moreover, carried out under aerobic conditions such as with shaking or stirring under aeration. These procedures can bring about satisfactory contact between the saturated hydrocarbon used as the starting compound, the liquid culture medium and the air phase.

In the cultivation as described above, the said microorganism is grown in order to oxidize the said saturated hydrocarbon so that the said saturated dicarboxylic acid accumulates in the culture medium.

When D-biotin is introduced as a nutrient, and the said saturated hydrocarbon, together with another carbon source, such as D-sorbitol, the microorganism grows initially on the carbon source rather than on the saturated hydrocarbon. The resting cells medium is with D-biotin, and D-sorbitol, thus-grown microorganism then begins oxidation of the saturated hydrocarbon in the fermentation medium.

The said saturated dicarboxylic acid produced and accumulated in the medium can be recovered and isolated. For instance, extraction with an organic solvent or precipitation by adjustment of the pH value of the liquid culture medium are generally employed. The liquid culture medium can be, if necessary, treated by an appropriate method, such as centrifuging or filtration, to remove the microorganism. The thus-treated liquid culture medium is then subjected to an appropriate procedure, such as extraction with diethyl ether, or the like, after acidification, so as efficiently to isolate the said desired product.

The said saturated dicarboxylic acid product can be identified as follows. The liquid culture medium or the reaction liquid is made alkaline with potassium hydroxide in order to dissolve the saturated dicarboxylic acid. The solution is taken and acidified with concentrated hydrochloric acid and extracted with diethyl ether. The ether extract is then treated with diazomethane for methylation, which is then subjected to analysis by gas chromatography and GC-MS (gas chromatography and mass spectrum measurement).

As described hereinbefore, the invention thus provides a process for the preparation of said saturated dicarboxylic acids that at present can be prepared only with difficulty by synthetic methods, wherein a microbiological process is applied to an said saturated hydrocarbon.

The salient feature of this invention resides in that, four yeasts belonging to Candida vini, Candida entamophila, Candida blankii and Pichia farinose which are capable of assimilating straight-chain hydrocarbons in a liquid medium containing a straight-chain hydrocarbon as a substrate to obtain a fermentation broth containing a long-chain dicarboxylic acid corresponding to said hydrocarbon.

All relevant microbial strains are described in Table 1.

TABLE 1

List of microbial strains discovered for there ability to produce long-chain dicarboxylic acid in a liquid medium containing a straight-chain saturated hydrocarbon (tridecane) as substrate.

| STRAIN | GENOTYPE | SOURCE |
| --- | --- | --- |
| MTCC246 | Wild-type | Microbial Type Culture Collection, IMTECH, Sector 39-A, Chandigarh. 160036, INDIA |
| MTCC1387 | Wild-type | Microbial Type Culture Collection, IMTECH, Sector 39-A, Chandigarh. 160036, INDIA |
| MTCC1030 | Wild-type | Microbial Type Culture Collection, IMTECH, Sector 39-A, Chandigarh. 160036, INDIA |
| MTCC624 | Wild-type | Microbial Type Culture Collection, IMTECH, Sector 39-A, Chandigarh. 160036, INDIA |

Materials and Methods

Microorganisms: n-alkane utilizing as well as dicarboxylic acid producing organisms were screened from the culture stocks. 4 out of 75 species screened were positive for production of said dicarboxylic acid from n-alkanes. Pichia farinose, Candida vini, candida entamophila, candida blankii were screened for production of brassylic acid from tridecane.

MEDIA: The following media are employed.

Medium A: Growth Medium for Microorganisms.

3.0 g yeast extract, 3.0 g malt extract, 5.0 g Peptone, 10 g Glucose and 1 L Distilled water, pH 7.0.

Medium B: Testing for Medium Production of Dicarboxylic Acid.

10 g $(NH_4)_2HPO_4$, 2 g $K_2HPO_4$, 0.3 g $MgSO_4$, 10 mg $FeSO_4.7H_2O$, 8 mg $ZnSO_4.7H_2O$, 8 mg $MnSO_4$, 9 ml Tridecane and 900 ml Distilled water, pH 7.0.

Medium D: Preparation of Resting Cells and Seed Culture for Fermentation Experiments.

20 g D-Sorbitol, 10 g $(NH_4)_2HPO_4$, 2 g $K_2HPO_4$, 0.3 g $MgSO_4$, 10 mg $FeSO_4.7H_2O$, 8 mg $ZnSO_4.7H_2O$, 8 mg $MnSO_4$, 2 g Yeast extract, 100 µg of Biotin and 900 ml Distilled water, pH 7.0.

Medium E: Fermentation Medium for Production of Dicarboxylic Acid.

Tridecane 5% v/v, Sodium acetate 5 g, $K_2HPO_4$ 2 g, $MgSO_4$ 0.3 g, $FeSO_4.7H_2O$ 10 mg, $ZnSO_4.7H_2O$, 8 mg, $MnSO_4$ 8 mg, Yeast extract 2 g and Distilled water 900 ml, pH 7.0.

Cultivation

Medium A is for growing microorganisms. The said microorganisms were transferred to medium A from slant and incubated at 30° C. for 2 days at 200 rpm on shaker. 10 ml of the inoculum is transferred from medium A to 100 ml of medium B in 500 ml flask, the cultivation was carried out at 30° C. for 2 days at 200 rpm on shaker, to check the production of dicarboxylic acid. For preparation of resting cells, 10 ml of inoculum was transferred from medium B to 200 ml of medium D in 500 ml conical flask, cultivation is carried at 30° C. for 2 days at 200 rpm. After culturing on a rotary shaker at 200 rpm for 2 days, the medium D with the said organism is centrifuged at 8,000 rpm for 10 min, and the cell pellet is collected. The cell pellet of the said yeasts obtained is transferred to medium-E, fermentation medium for the production of said dicarboxylic acid from liquid medium with said saturated hydrocarbon as substrate.

The microorganisms usable in this invention are those belonging to *Candida vini, Candida entamophila, Candida blankii* and *Pichia farinose* having an ability to produce long-chain dicarboxylic acids from straight-chain hydrocarbons. Another object of this invention is to produce increased yields of the said dicarboxylic acid from the straight-chain hydrocarbons using the said microorganisms with inducers. Inducers such as $H_2O_2$, alkanes, combination of $H_2O_2$ and alkanes are used for increasing the yields for the production the said dicarboxylic acid from liquid medium with saturated hydrocarbon as substrate.

Long-chain dicarboxylic acid producing yeasts belonging to *Candida vini, Candida entamophila, Candida blankii* and *Pichia farinose* are inoculated into and cultured in a medium containing as substrate a straight-chain saturated hydrocarbon, particularly one having a carbon number of 13, by adjusting the pH of the medium within the range of 6.0 to 7.0 in the initial stage of culture and then at of 7.0 in the remaining course of culture. The pH is preferably adjusted by addition of a neutralizing agent, such as ammonia, sodium hydroxide or potassium hydroxide, thereby producing in a high yield a long-chain dicarboxylic acid corresponding to the hydrocarbon used as substrate of the medium. As means for addition of a hydrocarbon (as substrate) and alkaline material, they may be added simultaneously by previously mixing and forming them into an emulsion by a suitable method or they may be added separately from each other. The cultivation is, moreover, carried out under aerobic conditions such as with shaking or stirring under aeration. These procedures can bring about satisfactory contact between the saturated hydrocarbon used as the starting compound, the liquid culture medium and the air phase.

When D-biotin is introduced as a nutrient, and the said saturated hydrocarbon, together with another carbon source, such as D-sorbitol, the microorganism grows initially on the carbon source rather than on the saturated hydrocarbon. The resting cells medium is with D-biotin, and D-sorbitol, thus-grown microorganism then begins oxidation of the saturated hydrocarbon in the fermentation medium.

By performing culture of said dicarboxylic acid producing yeasts in said medium by adjusting the pH of the medium to 6.0 to 7.0 in the initial stage of culture, it is possible to prevent impairment of the dicarboxylic acid producing ability of said yeasts which may be caused by mixing and growth of other contaminated microorganisms in the medium in the course of culture. The period in which the culture of said dicarboxylic acid producing yeasts is to be performed by maintaining the medium pH at from start of culture.

In the cultivation described above, the microorganism is grown in order to oxidize the said saturated hydrocarbon so that the said saturated dicarboxylic acid accumulates in the culture medium.

The liquid culture medium is extracted with hexane to remove the matters existing in admixture with the long-chain dicarboxylic acid in the fermentation broth such as unreacted hydrocarbon, by-products such as monocarboxylic acid, are effectively removed leaving the said dicarboxylic acid in the said broth and then an alkaline solution such as sodium hydroxide or potassium hydroxide is added to the fermentation broth obtained by said culture to adjust pH of the solution to 10 to 13, preferably 11 to 12, to dissolve the dicarboxylic acid in said fermentation broth. The said fermentation broth, is adjusted to pH 2.0, Suitable examples of strong mineral acids include, but are not limited to, hydrochloric acid, sulfuric acid, phosphoric acid, and bromic acid, to precipitate the dissolved dicarboxylic acid and extracted with ether in which the long-chain dicarboxylic acid substantially exists in the dissolved state.

The obtained product was determined by gas chromatography.

| GC assay procedure | | | | | | |
|---|---|---|---|---|---|---|
| | | | Retention time (min) | | | |
| Column | | | Tridecane | Dodecanol | Tridecanol | Methyl Brassylate |
| Packed column | Apizon-L | Col. Temp. = 190° C. Final temp. = 250° C. 12.5° C./min ramping. | 5.6 | 9.2 | 14.0 | 27.1 |
| Capillary column | SE 52 | Column temp = 200° C. | 1.5 | 1.7 | 2.0 | 4.1 |

GC conditions were standardized on packed column and capillary column

The Scheme for Alkane oxidation pathway is given below.

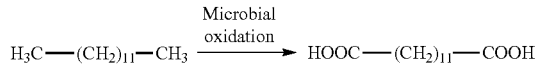

$$H_3C-(CH_2)_{11}-CH_3 \xrightarrow{\text{Microbial oxidation}} HOOC-(CH_2)_{11}-COOH$$

The present invention is now further described more in detail by reference to the following illustrative examples.

EXAMPLE 1

Production of Brassylic Acid by Fermentation of Tridecane with *Pichia farinosa*

One loopful of *Pichia farinose* (MTCC246), from nutrient medium slant were transferred to medium A, and incubated at 30 .degree. C. for 2 days at 200 rpm on a rotary shaker. 10 ml of the inoculum was transferred from medium A to 100 ml of medium B in 500 ml flask, the cultivation was carried out at 30 .degree. C. for 2 days at 200 rpm on shaker, this is to check the production of dicarboxylic acid. For preparation of resting cells, 10 ml of inoculum was transferred from medium B to 200 ml of medium D in 500 ml conical flask, cultivation is carried at 30 .degree. C. for 2 days at 200 rpm.

One aspect of the present invention provides a process for increasing the yields of the said dicarboxylic acid from the straight-chain hydrocarbons using the said microorganism is by using inducers. 0.1% $H_2O_2$ and 0.1% alkane were used as Inducers in medium D. After culturing on a rotary shaker at 200 rpm for 2 days, the medium D with the said organism is centrifuged at 8,000 rpm for 10 min. 10.08 gm (for 200 ml of medium D), of Cell pellet was obtained after centrifugation of the said broth with said yeast. All mediums were sterilized at 121° C. for 20 minutes.

The cell pellet of the said yeast obtained is transferred to medium-E, fermentation medium with 5% (v/v) of said saturated hydrocarbon (tridecane) for the production of said dicarboxylic acid (Brassylic acid) from liquid medium.

The carbon source is preferably maintained in contact with the aqueous phase and the microorganism. The oxidation is carried out at room temperature. A temperature in the range of 20° C.-35° C. is preferred. The pH of the medium is within the range of 6.0 to 7.0 in the initial stage of culturing and then at 7.0 in the succeeding state of culturing, the pH is preferably adjusted by addition of a neutralizing agent, such as ammonia, sodium hydroxide or potassium hydroxide.

The liquid culture medium is extracted with hexane to remove the matters existing in admixture with the long-chain dicarboxylic acid in the fermentation broth such as unreacted hydrocarbon, by-products such as monocarboxylic acid, are effectively removed leaving the said dicarboxylic acid in the said broth and then an alkaline solution such as sodium hydroxide or potassium hydroxide is added to the fermentation broth obtained by said culture to adjust pH of the solution to 10 to 13, preferably 11 to 12, to dissolve the dicarboxylic acid in said fermentation broth. The said fermentation broth, is adjusted to pH 2.0, Suitable examples of strong mineral acids include, but are not limited to, hydrochloric acid, sulfuric acid, phosphoric acid, and bromic acid, to precipitate the dissolved dicarboxylic acid and extracted with ether in which the long-chain dicarboxylic acid substantially exists in the dissolved state.

The obtained product was determined by gas chromatography and was confirmed by GC-MS. As the GC-MS data of the product agreed with that of the authentic sample, the product was identified as brassylic acid.

*Pichia farinose* produces 3876.71 mg/L of brassylic acid by oxidation of tridecane with 73.81% Selectivity and the percentage of conversion is 21.59.

EXAMPLE 2

Production of Brassylic Acid by Fermentation of Tridecane with *Candida vini*

One loopful of *Candida vini* (MTCC1387), from nutrient medium slant were transferred to medium A. Cultivation was carried out by incubating at 30° C. for 2 days at 200 rpm on a rotary shaker. Cultivation is carried in the same procedure as described in Example 1.

According to the present invention, increasing the yields of the said dicarboxylic acid from the straight-chain hydrocarbons using the said microorganism is by using 0.1% alkane as Inducers in medium D. After culturing on a rotary shaker at 200 rpm for 2 days, the medium D with the said organism is centrifuged at 8,000 rpm for 10 min. 3.098 gm (for 200 ml of medium-D), of Cell pellet was obtained after centrifugation of the said broth with said yeast. All mediums were sterilized at 121° C. for 20 minutes.

The cell pellet of the said yeast obtained is transferred to medium-E, fermentation medium with 5% (v/v) of said saturated hydrocarbon for the production of said dicarboxylic acid from liquid medium.

Extraction of the liquid culture broth for isolation of said dicarboxylic acid is carried in the same procedure as described in Example 1.

The obtained product was determined by gas chromatography and was confirmed by GC-MS. As the GC-MS data of the product agreed with that of the authentic sample, the product was identified as brassylic acid.

*Candida vini*, Produces 351.86 mg/L of brassylic acid by oxidation of tridecane with 99.18% Selectivity and the percentage of conversion is 2.80.

EXAMPLE 3

Production of Brassylic Acid by Fermentation of Tridecane with *Candida entamophila*

One loopful of *Candida entamophila* (MTCC1030), from nutrient medium slant were transferred to medium A. Cultivation was carried out at 30° C. for 2 days at 200 rpm on a rotary shaker. Cultivation is carried in the same procedure as described in Example 1.

According to the present invention, increasing the yields of the said dicarboxylic acid from the straight-chain hydrocarbons using the said microorganism is by using 0.1% $H_2O_2$ and 0.1% Alkane as Inducers in medium D. After culturing on a rotary shaker at 200 rpm for 2 days, the medium D with the said organism is centrifuged at 8,000 rpm for 10 min. 6.79 gm (for 200 ml of medium-D) of Cell pellet was obtained after centrifugation of the said broth with said yeast. All mediums were sterilized at 121° C. for 20 minutes.

The cell pellet of the said yeast obtained is transferred to medium-E, fermentation medium with 5% (v/v) of said saturated hydrocarbon for the production of said Dicarboxylic acid from liquid medium.

Extraction of the liquid culture broth for isolation of said dicarboxylic acid is carried in the same procedure as described in Example 1. The obtained product was determined by gas chromatography and was confirmed by GC-MS. As the GC-MS data of the product agreed with that of the authentic sample, the product was identified as brassylic acid.

*Candida entamophila*, Produces 778.02 mg/L of brassylic acid by oxidation of tridecane with 23.58% Selectivity and the percentage of conversion is 28.70.

EXAMPLE 4

Production of Brassylic Acid by Fermentation of Tridecane with *Candida blankii*

One loopful of *Candida blankii* (MTCC 624), from nutrient medium slant were transferred to medium A. And Cultivation was carried as incubated at 30° C. for 2 days at 200 rpm on a rotary shaker. Cultivation is carried in the same procedure as described in Example 1.

According to the present invention, increasing the yields of the said dicarboxylic acid from the straight-chain hydrocarbons using the said microorganism is by using 0.1% $H_2O_2$ and 1% Alkane as Inducers in medium D. After culturing on a rotary shaker at 200 rpm for 2 days, the medium D with the said organism is centrifuged at 8,000 rpm for 10 min. 6.79 gm (for 200 ml of medium-D), of Cell pellet was obtained after centrifugation of the said broth with said yeast. All mediums were sterilized at 121° C. for 20 minutes.

The cell pellet of the said yeast obtained is transferred to medium-E, fermentation medium with 5% (v/v) of said saturated hydrocarbon for the production of said dicarboxylic acid from liquid medium.

Extraction of the liquid culture broth for isolation of said dicarboxylic acid is carried in the same procedure as described in Example 1.

The obtained product was determined by gas chromatography and was confirmed by GC-MS. As the GC-MS data of the product agreed with that of the authentic sample, the product was identified as brassylic acid.

*Candida blankii*, produces 274.09 mg/L of brassylic acid by oxidation of tridecane with 45.68% Selectivity and the percentage of conversion is 5.22.

Table showing % Conversion and Selectivity of yeast for production of brassylic acid from Tridecane

| Culture no | Species | Yield mg/L | Inducers | % Selectivity | % Conversion |
| --- | --- | --- | --- | --- | --- |
| MTCC246 | *Pichia farinose* | 3876.71 | 0.1% $H_2O_2$ | 73.81 | 21.59 |
| MTCC1387 | *Candida vini* | 351.86 | 0.1% alk | 99.18 | 2.80 |
| MTCC1030 | *Candida entamophila* | 778.02 | 1% $H_2O_2$ + 0.1% alk | 23.58 | 28.70 |
| MTCC624 | *Candida blankii* | 274.09 | 0.1% $H_2O_2$ + 1% hex | 45.68 | 5.22 |

The Main Advantages of Present Invention are:

Aliphatic long-chain $\alpha,\omega$-dicarboxylic acids (DC) which can be produced by the microbial oxidation of n-alkanes are widely used as raw materials to synthesize products such as perfumes, polymers, adhesive, macrolid antibiotics and high quality lubricants In pharmaceutical applications, 1,13-dicarboxylic acid is valuable for preparation of synthetic muscone, an active ingredient in traditional Chinese medicine for treating coronary heart disease and inflammation of joints. The natural muscone is usually extracted from the scent glands of the adult male musk deers. Using chemical routes for the synthesis of long-chain alpha, omega dicarboxylic acids result in mixtures containing shorter chain lengths. As a result, extensive purification steps are necessary hence growing interest shown lately for the method of producing such long-chain dicarboxylic acids according to a fermentation process by utilizing the microorganisms. The salient feature of this invention resides in that, four yeasts belonging to *Candida vini, Candida entamophila, Candida blankii* and *Pichia farinosa* are screened capable of assimilating straight-chain hydrocarbons in a liquid medium containing a straight-chain hydrocarbon (tridecane) as a substrate to obtain a fermentation broth containing a long-chain dicarboxylic acid corresponding to said hydrocarbon.

Another advantage of the present invention is to produce increased yields of the said dicarboxylic acid from the straight-chain hydrocarbons using the said microorganisms with Inducers. Inducers such as $H_2O_2$, Alkanes, combination of $H_2O_2$ and Alkanes, Alkane are used for increasing the yields for the production of the said dicarboxylic acid from liquid medium with saturated hydrocarbon as substrate.

We claim:

1. A process for the preparation of one or more saturated dicarboxylic acids from one or more corresponding saturated hydrocarbons with the same number of carbon atoms and wherein the stereostructure of the saturated hydrocarbons is maintained, comprising culturing a microorganism strain selected from the group consisting of *Candida vini, Candida entamophila, Candida blankii* and *Pichia farinosa* in a liquid fermentation medium containing the one or more saturated hydrocarbons as substrate wherein one or more yield inducers selected from the group consisting of $H_2O_2$, alkanes, and mixtures thereof are added to the liquid fermentation medium in an amount effective for increasing the yield of saturated dicarboxylic acids.

2. The process according to claim 1, wherein a concentration of the saturated hydrocarbon substrate used is between 5-15% (v/v).

3. The process according to claim 1, wherein the liquid fermentation medium contains metal salts and organic cofactors.

4. The process according to claim 1, wherein the saturated hydrocarbon used is a straight chain hydrocarbon with 13 carbon atoms and with a methyl group at both the terminals.

5. The process according to claim 4, in which said saturated hydrocarbon used is tridecane and the corresponding saturated dicarboxylic acid produced is Brassylic acid.

6. The process according to claim 1, in which said saturated hydrocarbon used is tridecane and the corresponding saturated dicarboxylic acid produced is Brassylic acid wherein the culturing is effected under aerobic conditions.

7. The process according to claim 1 in which said saturated hydrocarbon used is tridecane and the corresponding saturated dicarboxylic acid produced is Brassylic acid wherein the microorganism strain is *Pichia farinosa* and selectivity with *Pichia farinosa* for the brassylic acid by oxidation of the tridecane is 73.81% and percentage of conversion is 21.59.

8. The process according to claim 1 in which said saturated hydrocarbon used is tridecane and the corresponding saturated dicarboxylic acid produced is Brassylic acid wherein the microorganism strain is *Candida blankii* and selectivity with *Candida blankii* for the brassylic acid by oxidation of the tridecane is 45.68% and percentage of conversion is 5.22.

9. The process according to claim 1 in which said saturated hydrocarbon used is tridecane and the corresponding saturated dicarboxylic acid produced is Brassylic acid wherein the microorganism strain is *Candida vini* and selectivity with *Candida vini*, for brassylic acid by oxidation of tridecane is 99.18% and percentage of conversion is 2.80.

10. The process according to claim 1 in which said saturated hydrocarbon used is tridecane and the corresponding saturated dicarboxylic acid produced is Brassylic acid wherein the *Candida entamopila* selectivity for brassylic acid by oxidation of the tridecane is 23.58% and percentage of conversion is 28.70.

11. The process according to claim 1 further comprising the steps of:
   (i) culturing the microorganism strain in a growth medium for microorganisms in the presence of a carbon source selected from n-decane and n-dodecane;
   (ii) transferring inoculum from the growth medium for microorganisms in step (i) to a testing medium for production of dicarboxylic acid and culturing;
   (iii) transferring inoculum cultivated in the testing medium of step (ii) to a medium for preparation of resting cells and seed culture in the presence of the one or more inducers to cultivate resting cells;
   (iv) centrifuging the medium for preparation of resting cells and seed culture of step (iii) to obtain cell pellet of the microorganism strain;

(v) transferring the cell pellet obtained in step (iv) to a fermentation medium for production of dicarboxylic acid and culturing in presence of the saturated hydrocarbon substrate.

12. The process according to claim 11, wherein in step (i) the growth medium for microorganisms comprises 3.0 g yeast extract, 3.0 g malt extract, 5.0 g Peptone, 10 g Glucose and 1 L Distilled water.

13. The process according to claim 11, wherein in step (ii) the testing medium for production of dicarboxylic acid comprises 10 g $(NH_4)_2HPO_4$, 2 g $K_2HPO_4$, 0.3 g $MgSO_4$, 10 mg $FeSO_4.7H_2O$, 8 mg $ZnSO_4.7H_2O$, 8 mg $MnSO_4$, 9 ml Tridecane and 900 ml Distilled water.

14. The process according to claim 11, wherein in step (iii) the medium for preparation of resting cells and seed culture comprises 20 g D-Sorbitol, 10 g $(NH_4)_2HPO_4$, 2 g $K_2HPO_4$, 0.3 g $MgSO_4$, 10 mg $FeSO_4.7H_2O$, 8 mg $ZnSO_4.7H_2O$, 8 mg $MnSO_4$, 2 g Yeast extract, 100 µg of Biotin and 900 ml Distilled water.

15. The process according to claim 11, wherein in step (v) the fermentation medium for production of dicarboxylic acid comprises Tridecane 5% v/v, Sodium acetate 5 g, $K_2HPO_4$ 2 g, $MgSO_4$ 0.3 g, $FeSO_4.7H_2O$ 10 mg, $ZnSO_4.7H_2O$ 8 mg, $MnSO_4$ 8 mg, Yeast extract 2 g and Distilled water 900 ml.

16. The process according to claim 11, wherein in step (v) the culturing comprises biochemical oxidation at a temperature between 20 to 35° C. for a period of up to 3 days and pH in the range of 6 to 7.

17. The process according to claim 11, wherein after culturing according to step (v), dicarboxylic acid is recovered from the fermentation medium.

18. The process according to claim 17, wherein after culturing, the fermentation medium is extracted with hexane to remove unreacted hydrocarbon, monocarboxylic acid and other unwanted matter, leaving dicarboxylic acid in fermentation broth, followed by addition of an alkaline solution comprising sodium hydroxide or potassium hydroxide to the fermentation broth to adjust pH of the solution to 10 to 13 to dissolve the dicarboxylic acid in said fermentation broth, followed by adjusting the pH of the fermentation broth to pH 2, using a mineral acid selected from the group consisting of hydrochloric acid, sulfuric acid, phosphoric acid, and bromic acid, to precipitate the dissolved dicarboxylic acid, followed by extraction of the dicarboxylic acid with ether.

19. The process according to claim 11, wherein the media in steps (ii), (iii) and (v) include one or more additional nutrients selected from the group consisting of a nitrogen source and an inorganic salt.

20. The process according to claim 19, wherein the nitrogen source is selected from the group consisting of peptone, urea, ammonium phosphate, ammonium chloride, ammonium sulfate and ammonium nitrate.

21. The process according to claim 19, wherein the inorganic salt is selected from the group consisting of phosphates, sulfates and hydrochlorides of sodium, potassium, magnesium, iron, nickel and zinc.

22. The process according to claim 20, wherein the inorganic salt is selected from the group consisting of $KH_2PO_4$, $K_2HPO_4$, $Na_2HPO_4.12H_2O$, $MgSO_4.7H_2O$, $FeSO_4.7H_2O$, $ZnSO_4.7H_2O$ and NaCl.

23. The process according to claim 11, wherein in step (iii) one or more nutrients selected from the group consisting of yeast extract, meat extract and D-biotin are added to the medium for preparation of the resting cells and seed culture.

24. A process for producing a saturated long-chain dicarboxylic acid which comprises culturing a yeast strain selected from the group consisting of *Candida vini, Candida entamophila, Candida blankii* and *Pichia farinosa*, capable of assimilating straight-chain hydrocarbons in a liquid medium containing a straight-chain hydrocarbon as a substrate to obtain a fermentation broth containing a long-chain dicarboxylic acid corresponding to said hydrocarbon, and recovering a saturated long chain dicarboxylic acid, wherein one or more yield inducers selected from the group consisting of $H_2O_2$, alkanes, and mixtures thereof are added to the liquid medium in an amount effective for increasing the yield of saturated dicarboxylic acids.

\* \* \* \* \*